US 6,610,738 B2

(12) United States Patent
Mihóknéet al.

(10) Patent No.: US 6,610,738 B2
(45) Date of Patent: Aug. 26, 2003

(54) N-DISUBSTITUTED CARBAMOYLOXY FLAVONES

(75) Inventors: Ildiko B. Mihókné, Debrecen (HU); György Tóth, Nyiregyháza (HU); Sándor Molnár, Debrecen (HU); Tivadar Tamás, Debrecen (HU); György Sulyok, Debrecen (HU); Eva K. Mudráné, Ebes (HU)

(73) Assignee: BIOGAL Pharmaceutical Co., Ltd., Debrecen (HU)

( * ) Notice: Subject to any disclaimer, the term of this patent is extended or adjusted under 35 U.S.C. 154(b) by 0 days.

(21) Appl. No.: 09/956,982

(22) Filed: Sep. 21, 2001

(65) Prior Publication Data

US 2002/0128494 A1 Sep. 12, 2002

Related U.S. Application Data

(60) Provisional application No. 60/234,239, filed on Sep. 21, 2000.

(51) Int. Cl.$^7$ ...................... A61F 31/352; C07D 311/22
(52) U.S. Cl. ........................................ 514/456; 549/403
(58) Field of Search ........................... 549/403; 514/456

(56) References Cited

U.S. PATENT DOCUMENTS

| 3,147,258 A | 9/1964 | Paola Da Re |
| 4,202,825 A | 5/1980 | Taya |

FOREIGN PATENT DOCUMENTS

| FR | 2 156 469 | 6/1973 |
| WO | 97 49693 | 12/1997 |

OTHER PUBLICATIONS

Chang et al., J. Chem. Soc., Article, p. 3414–3417 (1961).
Mahboobi, S., Pongratz, H., Synthesis of 2'–Amino–3'methoxyflavone (PD 98059), Synth. Commun., 1999; 9:1645.
Akama T., et a., Structure–activity relationships of the 7–substituents of 5,4'–diamino–6,8,3'–trifluoroflavone, a potent antitumor agent, J. Med. Chem., Jun. 4. 1998; 41(12):2056–67.
Rampa A., et al., Acetylcholinesterase inhibitors: synthesis and structure–activity relationships of omega–[N–methyl–N–(3–alkylcarbamoyloxyphenyl)methyl] aminoalkoxyheteroaryl derivatives, J. Med. Chem., Oct. 8, 1998; 41(21):3976–86.
van Acker SA, et al., Structural aspects of antioxidant activity of flavonoids. Free Radic. Biol. Med., 1996;20(3):331–42.
Varadarajan S. et al., Alzheimer's amyloid beta–peptide–associated free radical oxidative stress and neurotoxicity, J. Struct. Biol., Jun. 2000;130(2–3):184–208.
Pratico D, Delanty N., Oxidative injury in diseases of the central nervous system: focus on Alzheimer's disease, Am. J. Med., Nov. 2000; 109(7):577–85.
Giacobini E., Present and future of Alzheimer therapy, J. Neural. Transm. Suppl., 2000;59:231–42.
Aisen, PS., et al., Anti–inflammatory and antioxidant therapies in Alzheimer's disease, Funct. Neurobio. Aging, 487–492 (Hof and Mobbs edS., Academic Press: San Diego, California 2001.
Chemical Abstracts, vol. 74, No. 27, 1971 Columbus, Ohio, US; abstract No. 87763a, OWada, Etsuro et al.: "Synthesis of Alkyl or Aryl 7–Flavonyl Carbonates" p. 419; XP002190636 abstract & Nippon Kagaku Zasshi, vol. 91, No. 9, 1970, pp. 868–873, Tokyo.
Chemical Abstracts, vol. 98, No. 5, 1983 Columbus, Ohio, US; abstract No. 156357f, Rao, D. et al.: "On The Action of a Carbamate Analog as a Juvenile Hormone" p. 147; XP002190637 abstact & Curr. Sci., vol. 52, No. 3, 1983, pp. 142–143, Engl.
J. Org. Chem., 27,381 (1962).
PCT Search Report—International Application No.:PCT/US 01/29135 dated Mar. 7, 2002.
PCT Search Report—International Application No.: PCT/US 01/29579 dated Mar. 7, 2002.

*Primary Examiner*—Joseph K. McKane
*Assistant Examiner*—Kamal Saeed
(74) *Attorney, Agent, or Firm*—Venable LLP; Marina V. Schneller

(57) ABSTRACT

The invention relates to new flavone derivaties which have at least one N-disubstituted carbamoyloxy unit (OOCNR$^6$(R$^7$))coupled directly to one or both aromatic rings of the flavone molecule.

34 Claims, No Drawings

N-DISUBSTITUTED CARBAMOYLOXY FLAVONES

CROSS REFERENCE

This application relies on Provisional Application No. 60/234,239 filed on Sep. 21, 2000 which is relied upon and incorporated by reference herein.

FIELD OF THE INVENTION

The invention relates to novel flavones and to processes of making them.

BACKGROUND OF THE INVENTION

Flavonoids, such as flavones, are natural products produced by living organisms. Many of these compounds are natural products that do not appear to have any obvious metabolic or evolutionary function and may be formed by "metabolic accident" or are by-products of the synthetic machinery of the cellular enzymes. Regardless of their utility to the parent organism, their value to man as drugs, herbs, flavorings, poisons, dyes, and the like is undisputed.

The subject flavones comprise oxygenated derivatives of aromatic ring structures. Derivatives of flavone are found throughout the plant kingdom and especially in the higher plants. Although many biologically active flavone derivatives have been found in nature, they also have been produced synthetically. Certain of these compounds are useful as respiratory stimulants (U.S. Pat. No. 3,147,258), as an inhibitor of MAP kinase (Mahboobi, S., Pongratz, H., *Synthesis of 2'-Amino-3'methoxyflavone (PD 98059)*, Synth. Commun., 1999;29:1645), and as an antitumor agent (Akama T., et a., *Structure-activity relationships of the 7-substituents of 5,4'-diamino-6,8,3'trifluoroflavone, a potent antitumor agent*, J. Med. Chem., Jun. 4, 1998; 41(12) :2056–67). An acetylcholine esterase inhibitor compound was described in Rampa A., et al., *Acetylcholinesterase inhibitors: synthesis and structure-activity relationships of omega-[N-methyl-N-(3-alkylcarbamoyloxyphenyl) methyl] aminoalkoxyheteroaryl derivatives*, J. Med. Chem., Oct. 8, 1998; 41(21):3976–86, in which the flavone structure has a phenyl group bearing an N-methylcarbamoyloxy radical connected with the oxygen atom of the flavone skeleton via a five membered chain:

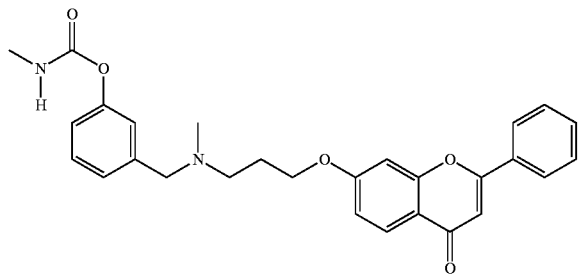

Flavonoids serve as antioxidants and chemoprotectants against molecular damage from reactive oxygen species (ROS). Their antioxidative activity has been the subject of many studies (e.g., van Acker SA, et al., *Structural aspects of antioxidant activity of flavonoids*, Free Radic. Biol. Med., 1996;20(3):331–42).

Oxidative stress, manifested by, for example. protein oxidation and lipid peroxidation is one characteristic of the brain of a person suffering from Alzheimer's Disease (AD) (Cf. Varadarajan S, et al., *Alzheimer's amyloid beta-peptide-associated free radical oxidative stress and neurotoxicity*, J. Struct. Biol., June 2000; 130(2–3):184–208. The beneficial effect of various antioxidants in the treatment of AD is now widely recognized. Cf. Pratico D, Delanty N., *Oxidative injury in diseases of the central nervous system: focus on Alzheimer's disease*, Am. J. Med., November 2000; 109(7) :577–85; Giacobini E., *Present and future of Alzheimer therapy*, J. Neural. Transm. Suppl., 2000; 59:231–42; Aisen, P S., et al., *Anti-inflammatory and antioxidant therapies in Alzheimer's disease*, Funct. Neurobio. Aging, 487–492 (Hof and Mobbs edS., Academic Press: San Diego, Calif. 2001). Various compounds incorporating a carbamoyl functionality (e.g., rivastigmine and physostigmine) are useful for the treatment of AD via enhancement of cholinergic transmission through inhibition of acetylcholinesterase (AChE).

The compounds of the present invention were designed as potential therapeutic agents for the treatment of AD by combining both ACHE inhibitory activity and antioxidant activity (by virtue of their carbamoyl and flavonoid pharmacophores).

SUMMARY OF THE INVENTION

The invention relates to compounds of the general Formula I:

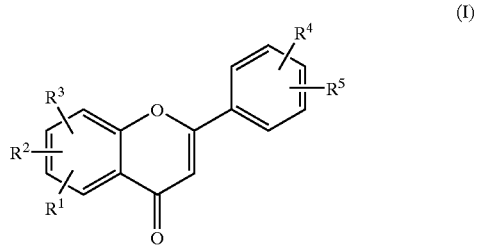

wherein each of $R^1$, $R^2$, $R^3$, $R^4$ and $R^5$ is a substituent selected from the group consisting of:

hydrogen;

$OOCNR^6(R^7)$, in which each of $R^6$ and $R^7$ is hydrogen, or a lower alkyl ($C_1$–$C_4$) and in which each of $R^6$ and $R^7$ may be the same or different;

$OR^8$, wherein $R^8$ is hydrogen or a lower alkyl ($C_1$–$C_4$);

wherein each of $R^9$ and $R^{10}$ is hydrogen or a lower alkyl ($C_1$–$C_4$);

a halogen atom selected from the group consisting of fluoride, chloride, bromide and iodide;

$COOR^{11}$, wherein $R^{11}$ is hydrogen, sodium, potassium, or a lower alkyl ($C_1$–$C_4$);

$CONR^{12}R^{13}$, wherein each of $R^{12}$ and $R^{13}$ is hydrogen or a lower alkyl ($C_1$–$C_4$);

$NO_2$; and $CN$; and wherein at least one of $R^1$, $R^2$, $R^3$, $R^4$ and $R^5$ is $OOCNR^6(R^7)$.

DETAILED DESCRIPTION OF THE INVENTION

The invention relates to new flavone derivatives of Formula I above which have at least one N-disubstituted carbamoyloxy unit (OOCNR$^6$(R$^7$)) coupled directly to one or both aromatic rings of the flavone molecule. Accordingly, the invention embraces compounds of Formulae IA, IB and IC, below. Compounds of Formula IA are characterized by the formula:

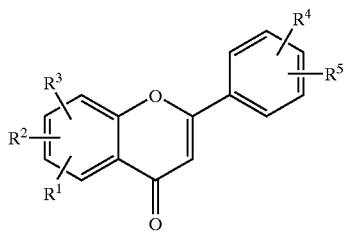
(IA)

wherein R$^4$ is OOCNR$^6$(R$^7$), in which each of R$^6$ and R$^7$ is hydrogen or a lower alkyl of 1 to 4 carbon atoms and in which each of R$^6$ and R$^7$ may be the same or different, and wherein R$^4$ occurs in the 2', 3' or 4' position; and
wherein each of R$^1$, R$^2$, R$^3$, and R$^5$ is a substituent selected from the group consisting of:
hydrogen;
OR$^8$, wherein R$^8$ is hydrogen or a lower alkyl of 1 to 4 carbon atoms,

wherein each of R$^9$ and R$^{10}$ is hydrogen or a lower alkyl (C$_1$–C$_4$);
a halogen atom selected from the group consisting of fluoride, chloride, bromide and iodide;
COOR$^{11}$, wherein R$^{11}$ is hydrogen, sodium, potassium, or a lower alkyl (C$_1$–C$_4$);
CONR$^{12}$R$^{13}$, wherein each of R$^{12}$ and R$^{13}$ is hydrogen or a lower alkyl (C$_1$–C$_4$);
NO$_2$; and
CN.

Compounds of Formula IB are characterized by the following formula:

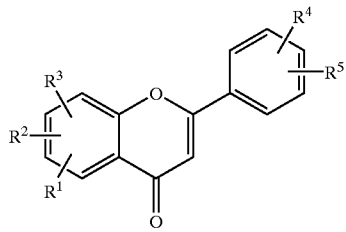
(IB)

wherein R$^1$ is OOCNR$^6$(R$^7$), in which each of R$^6$ and R$^7$ is hydrogen or a lower alkyl (C$_1$–C$_4$) and in which each of R$^6$ and R$^7$ may be the same or different, and wherein R$^1$ occurs in the 5, 6, 7, or 8 position; and wherein each of R$^2$, R$^3$, R$^4$ and R$^5$ is a substituent selected from the group consisting of:
hydrogen;
OR$^8$, wherein R$^8$ is hydrogen or a lower alkyl (C$_1$–C$_4$);

wherein each of R$^9$ and R$^{10}$ is hydrogen or a lower alkyl (C$_1$–C$_4$);
a halogen atom selected from the group consisting of fluoride, chloride, bromide and iodide;
COOR$^{11}$, wherein R$^{11}$ is hydrogen, sodium, potassium, or a lower alkyl (C$_1$–C$_4$);
CONR$^{12}$R$^{13}$, wherein each of R$^{12}$ and R$^{13}$ is hydrogen or a lower alkyl (C$_1$–C$_4$);
NO$_2$; and
CN.

The compounds of Formula IC are characterized by the following formula:

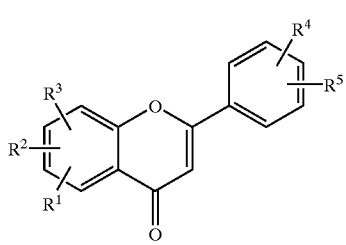
(IC)

wherein each of R$^1$ and R$^4$ is OOCNR$^6$(R$^7$) and R$^1$ occurs in the 5, 6, 7, or 8 position and R$^4$ occurs in the 2', 3', or 4' position, and each of R$^6$ and R$^7$ is hydrogen or a lower alkyl (C$_1$–C$_4$) and in which each of R$^6$ and R$^7$ may be the same or different; and
wherein each of R$^2$, R$^3$, and R$^5$ is a substituent selected from the group consisting of:
hydrogen;
OR$^8$, wherein R$^8$ is hydrogen or a lower alkyl (C$_1$–C$_4$);

wherein each of R$^9$ and R$^{10}$ is hydrogen or a lower alkyl (C$_1$–C$_4$);
a halogen atom selected from the group consisting of fluoride, chloride, bromide and iodide;
COOR$^{11}$, wherein R$^{11}$ is hydrogen, sodium, potassium, or a lower alkyl (C$_1$–C$_4$);
CONR$^{12}$R$^{13}$, wherein each of R$^{12}$ and R$^{13}$ is hydrogen or a lower alkyl (C$_1$–C$_4$);
NO$_2$; and
CN.

The definitions of each of R$^6$, R$^7$, R$^8$, R$^9$, R$^{10}$, R$^{11}$, R$^{12}$, R$^{13}$ indicates that each may be an alkyl of 1 to 4 carbon atoms, for example, methyl, ethyl, isopropyl, butyl, isobutyl or t-butyl.

Compounds of the invention are prepared by reacting a hydroxyflavone reactant with dialkylcarbamoyl chloride ($R^6R^7NCOCl$) in the presence of a base such as sodium hydride or potassium carbonate, according to the following reaction scheme:

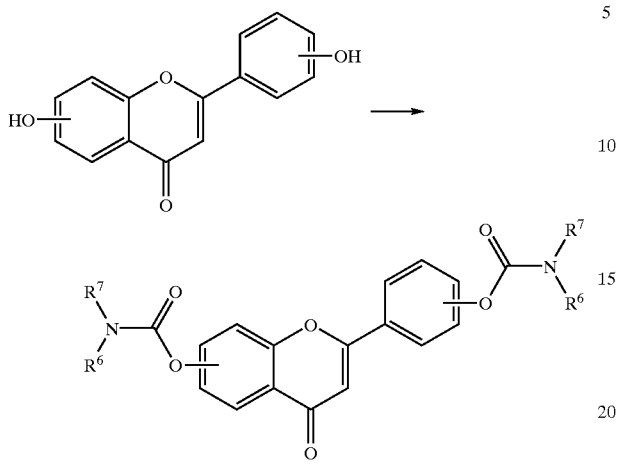

The reaction is carried out in an organic solvent such as dimethylformamide, acetonitrile or in a mixture of dimethylformamide and acetonitrile. The reaction can be undertaken at room temperature or up to about the boiling or reflux temperature of the solvent. For example, when the solvent contains acetonitrile, the reaction can be carried out at up to about 82° C., as determined by the boiling point of acetonitrile.

The hydroxyflavone reactant, used for production of the invention compounds in the reaction scheme set forth above, can be prepared by many methods. Various methods of hydroxyflavone synthesis are described in "The Chemistry of Flavonoid Compounds," Geissman, ed., Perg. Press (1962), which is relied upon and incorporated by reference herein. According to the synthetic method, shown below, the starting material is an appropriately substituted 2-hydroxyacetophenone derivative. The 2-hydroxyacetophenone derivative is the precursor for production of a phenolester derivative. In turn, the phenolester derivative is synthesized by reacting an aromatic acid chloride with the 2-hydroxyacetophenone derivative in a manner described, for example, in *Org. Synth. Coll.*, vol. IV, 478 (1963), which is relied upon and incorporated by reference herein. That phenolester is treated with alkali hydroxide(s) in pyridine to effect a Baker-Venkataraman rearrangement to produce a 1,3-diketone, as described in *J. Chem. Soc.*, 1381 (1933) and in *Curr. Sci.*, 4, 214 (1933), each of which is relied upon and incorporated by reference herein.

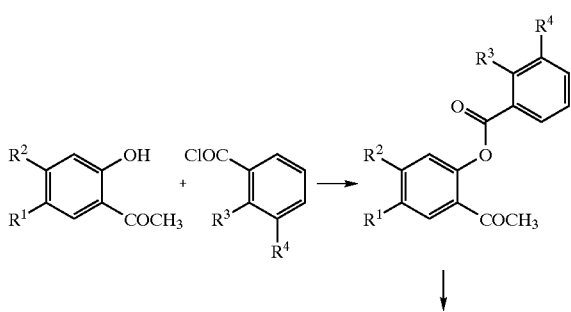

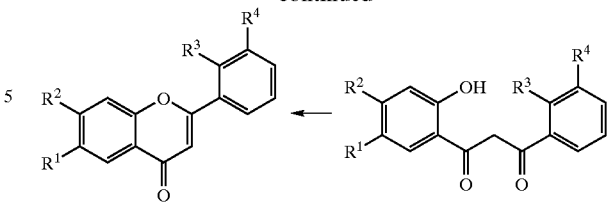

Ring closure of the 1,3-diketone, in the presence of mineral acid in acetic acid as a solvent, results in a flavone derivative having at least one alkoxy group. This compound is subjected to a dealkylation resulting in the desired hydroxyflavone compound as a precursor for the synthesis of new dialkylaminocarbamoyloxy derivatives of flavones.

Specific embodiments of the invention include compounds of Formula II:

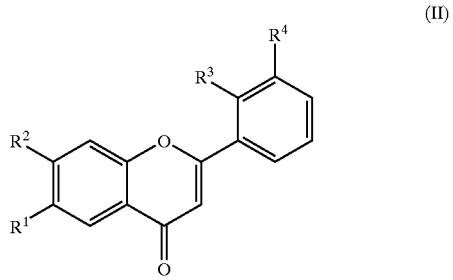

(II)

wherein $R^1$, $R^2$, $R^3$ and $R^4$ are selected from the group consisting of:

hydrogen;

$OOCNR^5(R^6)$, wherein each of $R^5$ and $R^6$ is a lower alkyl ($C_1$–$C_4$) and in which each of $R^5$ and $R^6$ may be the same or different;

$OR^7$, wherein $R^7$ is a lower alkyl ($C_1$–$C_4$);

wherein each of $R^8$ and $R^9$ is hydrogen or a lower alkyl ($C_1$–$C_4$);

a halogen atom selected from the group consisting of fluoride, chloride, bromide and iodide;

$COOR^{10}$, wherein $R^{10}$ is hydrogen, sodium, potassium, or a lower alkyl ($C_1$–$C_4$);

$CONR^{11}R^{12}$, wherein each of $R^{11}$ and $R^{12}$ is hydrogen, or a lower alkyl ($C_1$–$C_4$);

$NO_2$; and

CN; and wherein at least one of $R^1$, $R^2$, $R^3$ and $R^4$ is $OOCNR^5(R^6)$.

Specific compounds of Formula II are set forth in Table I:

TABLE I

| Example | $R^1$ | $R^2$ | $R^3$ | $R^4$ |
|---------|-------|-------|-------|-------|
| 1 | H | H | Me₂NCOO | H |
| 2 | H | H | Et, MeNCOO | H |
| 3 | H | H | H | Me₂NCOO |
| 4 | H | H | H | Et, MeNCOO |

TABLE I-continued
| Example | R¹ | R² | R³ | R⁴ |
|---|---|---|---|---|
| 5 | H | OEt | Me₂NCOO | H |
| 6 | H | OEt | Et, MeNCOO | H |
| 7 | H | Me₂NCOO | Ome | H |
| 8 | H | Me₂NCOO | Me₂NCOO | H |
| 9 | NH₂ | H | H | Me₂NCOO |
| 10 | NMe₂ | H | H | Me₂NCOO |
In the table, Me is methyl and Et is ethyl.
Compounds of Examples 1 and 2 below were prepared by the following synthetic route:
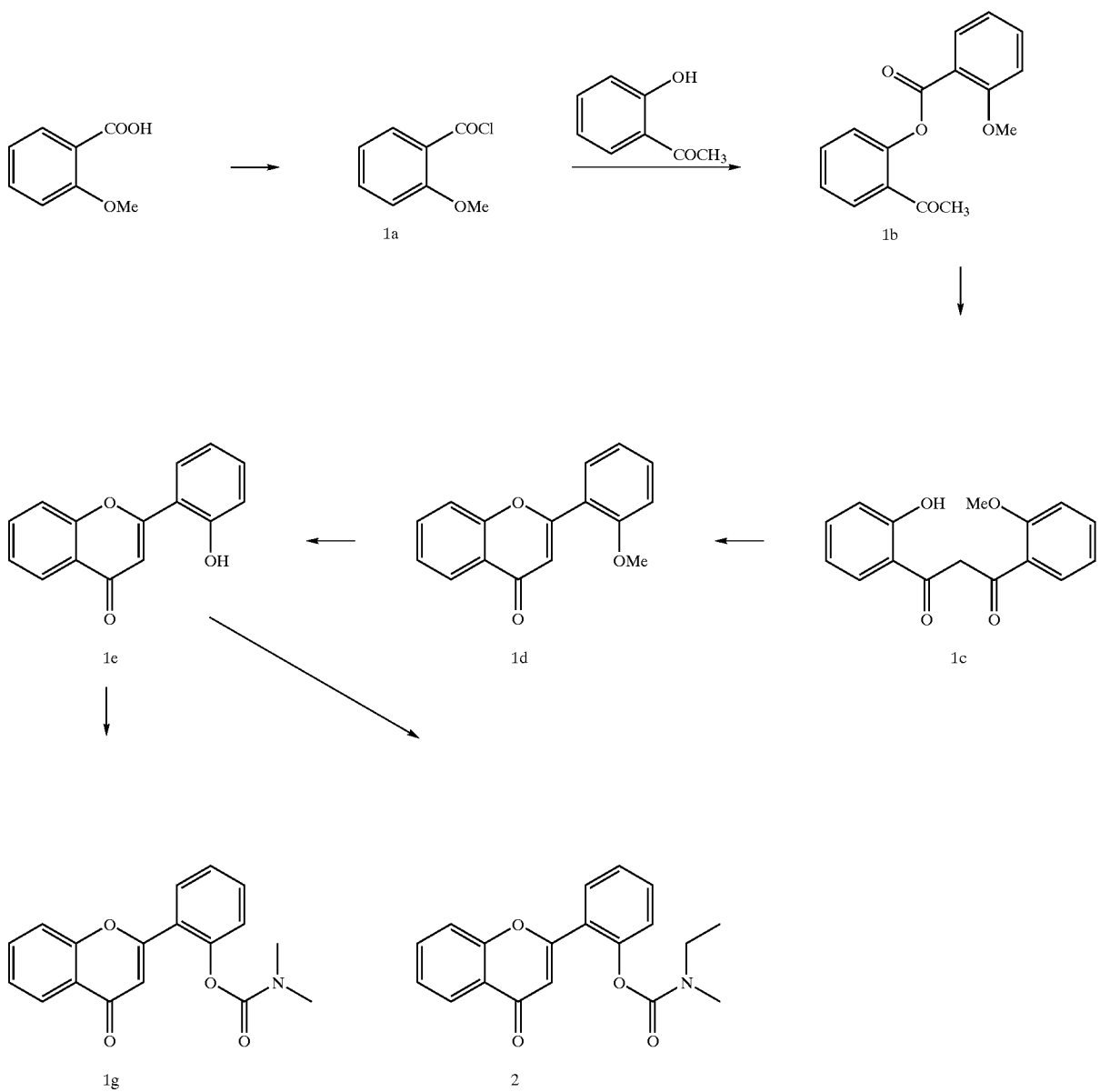

Compounds of Examples 5, 6, 7 and 8 below were prepared by the following synthetic route:
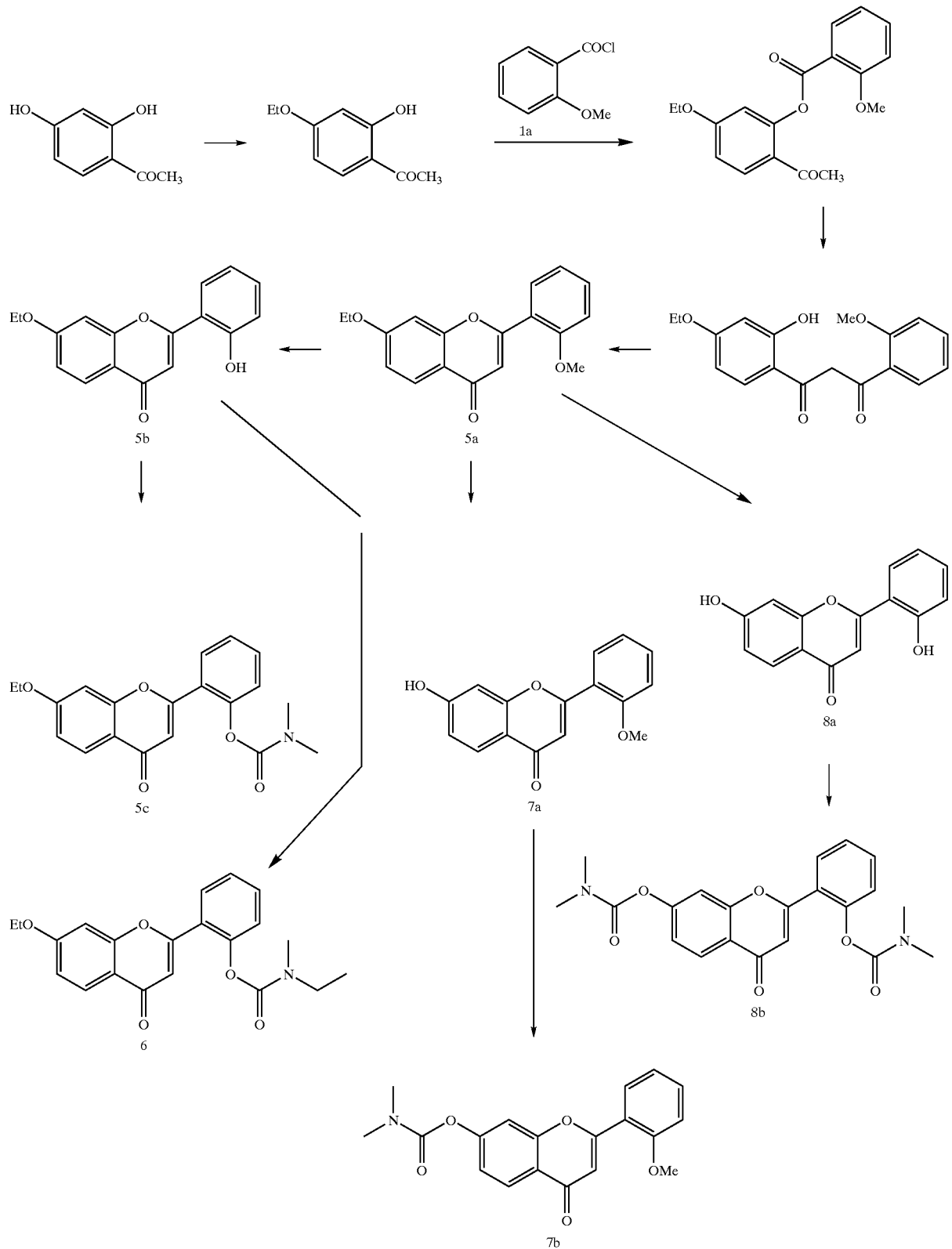

Compounds of Examples 9 and 10 below were prepared by the following synthetic route:
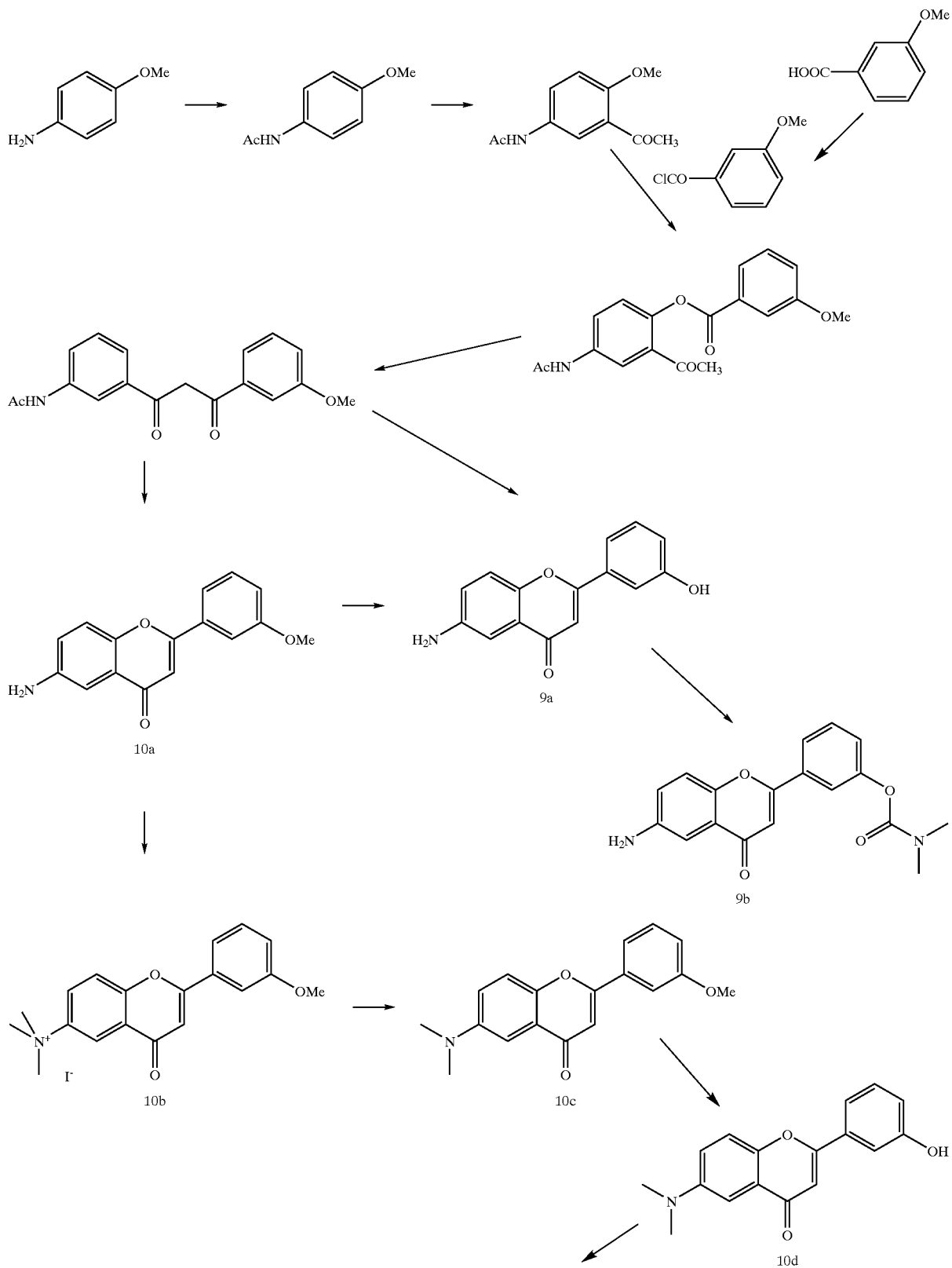

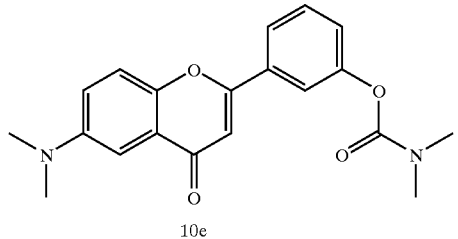

10e

Compounds of the invention were tested for acetylcholine esterase inhibition and did exhibit acetylcholine esterase inhibition. By way of background, acetylcholine may either increase muscle contraction (frog skeletal muscle) or decrease it (frog cardiac muscle) depending on the identity of the choline receptor affected and treated (*Molecular Biology*, Scientific American Books (Third Edition), p. 957 (1997)). During hydrolysis of acetylcholine by acetylcholine esterase, the acetyl group reacts with serine to produce toxins and inhibitors. Such toxins prolong the action of acetylcholine, prolonging the period of membrane depolarization. Such inhibitors can be lethal if they prevent relaxation of the muscles necessary for breathing (Id. at 965).

As pharmaceutical reagents, the carbamoyl derivatives of flavones of the invention can be compounded or diluted with pharmaceutically acceptable carriers and diluents, both liquid and solid, and formed into capsules or tablets for oral administration or formulated as solutions for parenteral administration, by intravenous or intramuscular administration. The invention also embraces inhibiting acetylcholine esterase activity by administering a compound of Formula I to a mammalian host in need of acetylcholine esterase inhibition.

The results of the acetylcholine esterase inhibitory activity testing are set forth in Table II:

TABLE II

| | AChE Activity of Flavone Derivatives | |
|---|---|---|
| | AChE inhibition | |
| structure | $IC_{50}(\mu M)$ | Ex vivo |
| | 2.65 | 29% at 40 $\mu M/kg$ |

TABLE II-continued

AChE Activity of Flavone Derivatives

| structure | AChE inhibition IC$_{50}$($\mu$M) | Ex vivo |
|---|---|---|
| [flavone with 3'-O-C(O)N(CH$_3$)$_2$ carbamate] | 1.4 | 42% at 40 $\mu$M/kg |
| [flavone with 3'-O-C(O)N(CH$_3$)(Et) carbamate] | 41 | |
| [flavone with 2'-O-C(O)N(CH$_3$)(Et) carbamate] | 3.5 | 14% at 50 $\mu$M/kg |
| [7-EtO flavone with 2'-O-C(O)N(CH$_3$)(Et) carbamate] | | |

TABLE II-continued

AChE Activity of Flavone Derivatives

| structure | AchE inhibition | |
|---|---|---|
| | IC$_{50}$(μM) | Ex vivo |
| [structure: 7-ethoxy-2-(2-(dimethylcarbamoyloxy)phenyl)-4H-chromen-4-one] | | |
| [structure: 7-(dimethylcarbamoyloxy)-2-(2-(dimethylcarbamoyloxy)phenyl)-4H-chromen-4-one] | | |
| [structure: 7-(dimethylcarbamoyloxy)-2-(2-methoxyphenyl)-4H-chromen-4-one] | | |
| [structure: 6-(trimethylammonio)-2-phenyl-4H-chromen-4-one chloride] | 10.5 (5') | |
| | 48 (30') | |
| [structure: 6-(trimethylammonio)-2-(4-methoxyphenyl)-4H-chromen-4-one chloride] | 5.5 (5') | |
| | 6 (30') | |

TABLE II-continued

AChE Activity of Flavone Derivatives
AchE inhibition

| structure | IC$_{50}$($\mu$M) | Ex vivo |
|---|---|---|
|  | 10 (5') | No inhibition at >50 Mmol/kg |
|  | 5.8 (30') |  |

The foregoing ex vivo results recommend application of therapeutically effective amounts of composition of the invention to mammalian hosts, including human hosts, to inhibit acetylcholine esterase activity, and diseases associated with such activity, for example, AD. The following examples are illustrative of the invention. However, the examples simply present specific embodiments of the invention. The invention embraces the subject matter of the appended claims and all equivalents thereof.

EXAMPLES

Example 1

2' (N,N-Dimethylcarbamoyloxy) Flavone

Example 1a

2-Methoxybenzoyl Chloride

A mixture of 2-methoxybenzoic acid (45.6 g, 0.3 mol), thionyl chloride (53.5 g, 33 ml, 0.45 mol) and dimethylformamide (two drops) was refluxed for an hour. Excess thionyl chloride was then distilled off under reduced pressure. Benzene (50 ml) was added to the residue and the solvent was distilled off until the weight of the residue remained unchanged (about 51 g).

Example 1b

2-[(2-Methoxybenzoyl)oxy]-acetophenone

2-Methoxybenzoyl chloride (about 51 g) from Example 1a was added dropwise to a mixture of 2-hydroxyacetophenone (27.2 g, 24.1 ml, 0.20 mol) and pyridine (40 ml). The reaction mixture was warmed to about 60° C. exothermically. After stirring for 15 minutes, the reaction mixture was poured onto a mixture of ice (800 g) and 36% hydrochloric acid (120 ml). The solid was filtered off, washed with water, and dried. The crude product was crystallized from methanol to yield 48.4 g (89.6%) of the compound (m.p.: 78–79° C.).

Example 1c 1-(2-Hydroxyphenyl)-3-(2-methoxyphenyl)-propan-1,3-dione

2-[(3-Methoxybenzoyl)oxy]-acetophenone (40.5 g, 0.15 mol) in pyridine (135 ml) was warmed to 50° C., and pulverized potassium hydroxide (12.6 g, 0.225 mol) was added to the solution gradually. The temperature of the reaction mixture rose spontaneously to 70–80° C. The mixture was mechanically stirred for 15 minutes, during which time a copious precipitate formed. The mixture was cooled to room temperature and acidified with 10% acetic acid (200 ml). The product was collected on a filter and washed with water and methanol. The yield was 29.3 g (72.3%) (m.p.: 80–84° C.).

Example 1d

2'-Methoxyflavone

A solution of 1-(2-hydroxyphenyl)-3-(2-methoxyphenyl)-propan-1,3-dione (27 g, 0.1 mol) in acetic acid (130 ml) and concentrated sulfuric acid (5 ml) were placed in a flask fitted with a reflux condenser and a stirrer. The flask was heated in a bath maintained at 100° C. for an hour. Then the reaction mixture was poured onto crushed ice (750 g). The solid was filtered off, washed with water, dried and crystallized from methanol to give 24.3 g (96.2%) of the compound (m.p.: 97–98.5° C.). In the literature (J. Org. Chem., 27, 381 (1962)), 102–103° C. is given for the product melting point.

Example 1e

2'-Hydroxyflavone from 2'-methoxy-flavone

A mixture of 2'-methoxyflavone (12.6 g, 0.05 mol), 33% hydrogen bromide in acetic acid (80 ml) and 47% hydrogen bromide in water (115 ml) was refluxed for 8 hours; then the mixture was left to cool to room temperature. The solid was isolated by filtration and washed with acetic acid, water and acetone to afford 11.0 g (92.3%) of the compound (m.p.: 248–249° C.). The literature (J. Org. Chem., 1962, 27, 381 (1962)) reports the product melting point as 246–247° C.

Example 1f

2'-Hydroxyflavone from 1-(2-hydroxyphenyl)-3-(2-methoxyphenyl)-propan-1,3-dione 1,3-Diketone (13.5 g, 0.05 mol) from Example 1c was used instead of 2'-methoxy-flavone and the compound was prepared according to the procedure described in Example 1e. The yield was 10.6 g (89.2%) (m.p.: 248–249° C.).

Example 1g

2'-(N,N-dimethylcarbamoyloxy)flavone

2'-Hydroxyflavone (2.38 g, 0.01 mol) was dissolved in dimethylformamide (100 ml), and 55–60% sodium hydride in mineral oil (0.48 g) was added to the solution. The reaction mixture was stirred at room temperature for an hour. N,N-dimethylcarbamoyl chloride (1.29 g, 1.10 ml, 0.012 mol) in dimethylformamide (5 ml) was added to the reaction mixture dropwise. The reaction mixture was stirred at room temperature for an hour. The inorganic salt was filtered off; and the filtrate was evaporated to dryness under reduced pressure. During the evaporation, the bath temperature was not allowed to exceed 65° C. The residue was dissolved in warm diethyl ether and treated with charcoal and aluminium oxide. The solution was evaporated to a small volume. The white crystals were collected by filtration, washed with petroleum ether (boiling range 40–60° C.) to afford 1.79 g (57.8%) of the compound (m.p.: 86.5–87.5° C.).
Analysis: calculated for $C_{18}H_{15}NO_4$: C, 69.89; H, 4.89; N, 4.53.
Found: C, 69.89; H, 4.73; N, 4.58.
IR (KBr): 1723, 1646 $cm^{-1}$ (CO).
$^1H$ NMR ($CDCl_3$): δ=2.97 (s, 3H), 3.09 (s, 3H), 6.69 (s, 1H), 7.2–8.3 (m, 8H).

Example 2

2'-(N-Ethyl-N-methylcarbamoyloxy)flavone

The crude compound was obtained, following the general procedure of Example 1g, from the reaction of 2'-hydroxyflavone (2.38 g, 0.01 mol), N-ethyl-N-methylcarbamoyloxy chloride (1.46 g, 0.12 mol) and sodium hydride. The crude product was purified by column chromatography (silica, 7:1 $CH_2Cl_2$/EtOAc as eluent) and crystallized from acetone-water. The yield was 1.52 g (47.0%) (m.p.: 68–70° C.).
Analysis: calculated for $C_{19}H_{17}NO_4$: C, 70.58; H, 5.30; N, 4.33.
Found: C, 70.45; H, 5.32; N, 4.29.
IR (KBr): 1712, 1640 $cm^{-1}$ (CO).
$^1H$ NMR ($CDCl_3$): δ=1.14 (dt, 3H), 3.00 (ds, 3H), 3.41 (dq, 2H), 6.67 (s, 1H), 7.2–8.3 (m, 8H).

Example 3

3'-(N,N-Dimethylcarbamoyloxy)flavone 2.38 g (0.01 mol) of 3'-hydroxyflavone (m.p.: 209–211° C.) prepared from 3-methoxybenzoic acid and 2-hydroxyacetophenone (according to Examples 1a, b, c, f)) and potassium carbonate (2.21 g, 0.016 mol), was stirred in a combined solvent of dimethylformamide (50 ml) and acetonitrile (20 ml). N,N-Dimethylcarbamoyl chloride (1.18 g, 1.0 ml, 0.11 mol) in acetonitrile (10 ml) was added to the reaction mixture over a period of 20 minutes. The reaction mixture was boiled under a reflux condenser for 3 hours then poured onto crushed ice (400 g) and neutralized with hydrochloric acid. The product was filtered off and washed with water to afford 2.89 g (93.4%) (m.p.: 125–126° C.).
Analysis: calculated for $C_{18}H_{15}NO_4$: C, 69.89; H, 4.89; N, 4.53.
Found: C, 69.76; H, 4.71; N, 4.41.
IR (KBr): 1718, 1654 $cm^{-1}$ (CO).
$^1H$ NMR ($CDCl_3$): δ=3.07 (s, 3H), 3.17 (s, 3H), 6.83 (s, 1H), 7.2–8.3 (m, 8H).

Example 4

3'-(N-Ethyl-N-methylcarbamoyloxy)flavone

Starting from 3'-hydroxyflavone (2.38 g, 0.01 mol), N-ethyl-N-methylcarbamoyl chloride (1.46 g, 0.012 mol) and 55–60% sodium hydride in mineral oil (0.48 g), the compound was synthesized utilizing the procedure of Example 1g to give 2.60 g (80.4%) (m.p.: 109–111° C.).
Analysis: calculated for $C_{19}H_{17}NO_4$: C, 70.58; H, 5.30; N, 4.33.
Found: C, 70.21; H, 5.03; N, 4.37.
IR (KBr): 1738, 1652 $cm^{-1}$ (CO).
$^1H$ NMR ($CDCl_3$): δ=1.22 (dt, 3H), 3.09 (ds, 3H), 3.50 (dq, 2H), 6.83 (s, 1H), 7.2–8.4 (m, 8H).

Example 5

7-Ethoxy-2'-(N,N-dimethylcarbamoyloxy)flavone

Example 5a

7-Ethoxy-2'-methoxyflavone 2,4-Dihydroxyacetophenone was alkylated with bromoethane in acetone in the presence of potassium carbonate to obtain 2-hydroxy-4-methoxyacetophenone. Using this compound and 2-methoxy-benzoic acid as starting materials, the syntheses according to Examples 1a, b, c, and d yielded the compound (m.p.: 153–154.5° C.).
IR (KBr): 1623 $cm^{-1}$ (CO).
$^1H$ NMR ($CDCl_3$): δ=1.49 (t, 3H), 3.94 (s, 3H), 4.15 (q, 2H), 6.8–8.2 (m, 8H).

Example 5b

7-Ethoxy-2'-hydroxyflavone

7-Ethoxy-2'-methoxyflavone (7.4 g, 0.025 mol) was agitated in dichloromethane (100 ml). Boron tribromide (9.4 g, 3.6 ml, 0.0375 mol) in dichloromethane (100 ml) was added dropwise for an hour. The agitation was continued at room temperature for 24 hours. The reaction mixture was poured onto a mixture of crushed ice (100 g) and 36% hydrochloric acid (10 ml). After stirring the mixture for an hour, the precipitate was filtered off. 2.15 g (29%) of unreacted 7-ethoxy-2'-methoxyflavone was recovered. The filtrate was evaporated under reduced pressure to remove dichloromethane. From the aqueous residue, crude 7-ethoxy-2'-hydroxyflavone was obtained by filtration. The crude product was dried, thoroughly pulverized and treated with boiling chloroform for half an hour. The undissolved product was collected by filtration from the cooled mixture; and the crude 7-ethoxy-2'-hydroxyflavone was crystallized from dimethylformamide to give 3.10 g (43.9%) (m.p.: 295–297° C.).
IR (KBr): 1624 $cm^{-1}$ (CO).
$^1H$ NMR (DMSO): δ=1.40 (t, 3H), 4.20 (q, 2H), 6.9–8.1 (m, 8H), 10.76 (s, 1H).

Example 5c

7-Ethoxy-2'-(N-dimethlylcarbamoyloxy) flavone

Using 7-ethoxy-2'-hydroxyflavone (2.82 g, 0.01 mol) as starting material, the compound was obtained according to Example 1g. The crude product was crystallized from methanol to give 1.25 g (35.4%) (m.p.: 166–168° C.).
Analysis: calculated for $C_{20}H_{19}NO_5$: C, 67.98; H, 5.42; N, 3.96
Found: C, 67.95; H, 5.29; N, 3.99.
IR (KBr): 1736, 1637 $cm^{-1}$ (CO).
$^1H$ NMR ($CDCl_3$): δ=1.50 (t, 3H), 2.99 (s, 3H), 3.10 (s, 3H), 4.14 (q, 2H), 6.67 (s, 1H), 6.8–8.2 (m, 7H).

Example 6

7-Ethoxy-2'-(N-ethyl-N-methylcarbamoyloxy) flavone

The experiment was conducted in a manner analogous to the procedure of Example 1g. 7-Ethoxy-2'-hydroxyflavone (2.82 g, 0.01 mol) and N-ethyl-N-methylcarbamoyl chloride (1.46 g, 0.012 mol) were used as starting materials. The crude title compound was crystallized from methanol to afford 1.35 g (36.7%) (m.p.: 91–93.5° C.).
Analysis: calculated for $C_{21}H_{21}NO_5$: C, 68.65; H, 5.76; N, 3.81.
Found: C, 68.30; H, 5.71; N, 3.80.
IR (KBr): 1731, 1643 $cm^{-1}$ (CO).
$^1$H NMR (CDCl$_3$): δ=1.14 (q, 3H), 1.49 (t, 3H), 3.03 (s, 3H), 3.42 (m, 2H), 4.13 (q, 2H), 6.5–8.3 (m, 8H).

Example 7

7-(N,N-Dimethylcarbamoyloxy)-2'-methoxyflavone

Example 7a

7-Hydroxy-2'-methoxyflavone

A mixture of 7-ethoxy-2'-methoxyflavone (8.89 g, 0.03 mol) and aluminum chloride (20 g, 0.15 mol) in dichloromethane (300 ml) was stirred at room temperature for 16 hours. The reaction mixture was poured onto a mixture of crushed ice (500 g) and 36% hydrochloric acid (50 ml). The precipitate formed was filtered off, washed with water, dried and the crude compound was crystallized from dimethylformamide to afford 6.0 g (74.6%) (m.p.: 260–264° C.).
IR (KBr): 1625 $cm^{-1}$ (CO).
$^1$H NMR (DMSO): δ=3.91 (s, 3H), 6.8 (s, 1H), 6.85–8.0 (m, 7H), 10.83 (s, 1H).

Example 7b 7-(N,N-Dimethylcarbamoyloxy)-2'-methoxyflavone

Starting from 7-hydroxy-2'-methoxyflavone (2.68 g, 0.01 mol), the compound was prepared using a procedure analogous to that of Example 1g. The crude product was crystallized from methanol to give 1.36 g (40.1%) (m.p.: 133.5–135° C.).
Analysis: calculated for $C_{19}H_{17}NO_5$: C, 67.25; H, 5.05; N, 4.13.
Found: C, 66.86; H, 4.90; N, 4.08.
IR (KBr): 1728, 1642 $cm^{-1}$ (CO).
$^1$H NMR (DMSO); δ=2.97 (s, 3H), 3.10 (s, 3H), 3.94 (s, 3H), 6.94 (s, 1H), 7.0–8.2 (m, 7H).

Example 8

7,2'-Di(N,N-dimethylcarbamoxyloxy)flavone

Example 8a 7,2'-Dihydroxyflavone

7-Ethoxy-2'-methoxyflavone (7.4 g, 0.025 mol) and boron tribromide (12.5 g, 4.4 ml, 0.05 mol) were added to dichloromethane (50 ml). The reaction mixture was refluxed for two hours and then cooled to room temperature. The solid was collected by filtration and washed with dichloromethane. The crude product was agitated in a mixture of cold water (100 ml) and 36% hydrochloric acid (10 ml) for half an hour. After filtration and washing with water, the wet product was dried and crystallized from dimethylformamide to afford 5.63 g (88.6%) (m.p.: 335–339° C.).
The literature (Berichte, 32, 1033(1899)) reports 320° C. as the melting point of this compound.
IR (KBr): 1618 $cm^{-1}$ (CO).
$^1$H NMR (DMSO); δ=6.80 (s, 1H), 6.85–8.0 (m, 7H), 10.67 (s, 1H), 10.80 (s, 1H).

Example 8b 7,2'-Di(N, N-dimethylcarbamoyloxy)flavone 7-2'-Dihydroxyflavone (5.09 g, 0.02 mol) and 55–60% sodium hydride in mineral oil (1.92 g) were added into dimethylformamide (200 ml). The mixture was stirred at room temperature for an hour. N,N-Dimethylcarbamoyl chloride (5.16 g, 4.4 ml, 0.048 mol) in dimethylformamide (20 ml) was added dropwise for 15 minutes. The reaction mixture was stirred at room temperature for 24 hours; then the solvent was distilled off under reduced pressure. Ice-cold water (200 g) was added to the residue and the pH was adjusted to 7.0 with 17% hydrochloric acid. The crude product was filtered off, washed with water, and crystallized from methanol and then acetone. The pure compound weighed 3.27 g (41.2%) (m.p.: 145.5–147° C.).
Analysis: calculated for $C_{21}H_{20}N_2O_6$: C, 63.63; H, 5.09; N, 7.07.
Found: C, 63.67; H, 5.05; N, 7.04.
IR (KBr): 1718, 1641 $cm^{-1}$ (CO).
$^1$H NMR (CDCl$_3$); δ=2.97 (s, 3H), 3.03 (s, 3H) 3.09 (s, 3H), 3.13 (s, 3H), 6.69 (s, 1H), 7.1–8.3 (m, 7H).

Example 9

6-Amino-3'-(N,N-dimethylcarbamoyloxy)flavone

Example 9a

6-Amino-3'-hydroxyflavone

N-Acetyl-p-anisidine (m.p.: 127–130° C.) was obtained from p-anisidine which was boiled in a mixture of acetic anhydride and acetic acid. 5-Acetamido-2-hydroxyacetophenone (m.p.: 165–167° C.) was synthesized by Friedel-Crafts reaction from N-acetyl-p-anisidine (J. Chem. Soc., 3414 (1961)). Starting from 3-methoxy-benzoic acid and 5-acetamido-2-hydroxyacetophenone, the compound, 6-amino-3'hydroxyflavone, was synthesized according to Examples 1a, b, c, and f. The compound melted at 265–268° C.
IR (KBr): 1620 $cm^{-1}$ (CO).
$^1$H NMR (DMSO); δ=5.52 (s, 2H), 6.75 (s, 1H), 6.9–7.6 (m, 7H), 9.89 (s, 1H).

Example 9b

6-Amino-3'-(N,N-dimethylcarbamoyloxy)flavone

The compound was produced from 6-amino-3'-hydroxyflavone (2.53 g, 0.01 mol) according to the procedure of Example 3. The crude compound was purified by column chromatography (silica, 3:1 EtOH/CHCl$_3$ as eluent) to yield 2.38 g (73.4%) (m.p.: 157–159° C.).
Analysis: calculated for $C_{18}H_{16}N_2O_4$: C, 66.66; H, 4.97; N, 8.64.
Found: C, 66.23; H, 4.87; N, 8.77.
IR (KBr): 1716, 1629 $cm^{-1}$ (CO).
$^1$H NMR (DMSO); δ=2.93 (s, 3H), 3.19 (s, 3H), 5.53 (s, 2H), 6.90 (s, 1H), 6.95–8.0 (m, 7H).

Example 10

6-Dimethylamino-3'-(N,N-dimethylcarbamoyloxy) flavone

Example 10a

6-Amino-3'-methoxyflavone 1-(2-Hydroxy-5-acetamidophenyl)-3-(3-methoxyphenyl)-propan-1,3-dione (98.2 g, 0.3 mol, m.p.:

72–73° C.) was synthesized from 5-acetamido-2-hydroxyacetophenone and 3-methoxybenzoic acid according to Examples 1a, b, and c. It was then added to a combined solution of acetic acid (300 ml) and 36% hydrochloric acid (150 ml). The reaction mixture was refluxed for 16 hours; then it was allowed to stand at room temperature for 16 hours. The product was isolated by filtration and washed with methanol. The wet product was agitated in water (1000 ml), and the pH was adjusted to 11 with 25% ammonium hydroxide. The product was filtered off and washed with water and ethanol to afford 75.4 g (94.0%) (m.p.: 203–206° C.).
IR (KBr): 1614 cm$^{-1}$ (CO).
$^1$H NMR (DMSO); δ=3.88 (s, 3H), 5.53 (s, 2H), 6.92 (s, 1H), 7.0–7.7 (m, 7H).

Example 10b

Trimethyl-6-(3'-methoxyflavonyl)ammonium iodide

A mixture of 6-amino-3'-methoxyflavone (53.5 g, 0.20 mol) and potassium carbonate (96.7 g, 0.70 mol) in dimethylformamide (1250 ml) was stirred at room temperature for half an hour. Iodomethane (99.4 g, 44 ml, 0.70 mol) was added and the reaction mixture was agitated at the same temperature for 8 days. The solid was filtered off, thoroughly washed with water, and dried. The yield was 73.6 g (84.1%) (m.p.: 189–191° C.).

Example 10c

6-Dimethylamino-3'-methoxyflavone

Trimethyl-6-(3'-methoxyflavonyl)ammonium iodide (43.7 g., 0.10 mol) in ethanol-amine (175 ml) was stirred at 70° C. for an hour. The reaction mixture was evaporated to dryness under reduced pressure. Methanol (100 ml) was added to the residue; and the solid was collected by filtration. The wet crude product was boiled in chloroform (80 ml) for 10 minutes; and the solid was filtered off from the hot suspension. Methanol (170 ml) was added to the filtrate; and the solution was concentrated to 100 ml under reduced pressure by distillation. After standing for 16 hours, the compound was collected by filtration and washed with methanol to give 12.4 g (42.0%) (m.p.: 169–170.5° C.).
IR (KBr): 1618 cm$^{-1}$ (CO).
$^1$H NMR (CDCl$_3$); δ=3.06 (s, 6H), 3.39 (s, 3H), 6.80 (s, 1H), 6.9–7.6 (m, 7H).

Example 10d

6-Dimethylamino-3-hydroxyflavone

6-Dimethylamino-3'-methoxyflavone (11.8 g, 0.04 mol) was added to a mixture of 33% hydrobromic acid in acetic acid (40 ml) and 47% hydrobromic acid in water (80 ml). The reaction mixture was refluxed for an hour and then cooled to 10° C. The crystals were filtered off and washed with water and ethanol. The crude compound was crystallized from a mixture of dimethylformamide and methanol to afford 9.35 g (83.2%) (m.p.: 233–235° C.).
IR (KBr): 1617 cm$^{-1}$ (CO).
$^1$H NMR (DMSO); δ=3.01 (s, 6H), 6.84 (s, 1H), 6.9–7.7 (m, 7H), 9.87 (s, 1H).

Example 10e

6-Dimethylamino-3'-(N,N-dimethylcarbamoyloxy) flavone

Using 6-dimethylamino-3'-hydroxyflavone as starting material (2.81 g, 0.01 mol), the reaction was conducted in a manner analogous to the process of Example 3. The crude title compound was crystallized from a mixture of chloroform and methanol to give 2.18 g (61.9%) (m.p.: 167–168° C.).
Analysis: calculated for $C_{20}H_{20}N_2O_4$: C, 68.17; H, 5.72; N, 7.95.
Found: C, 68.12; H, 5.65; N, 8.08.
IR (KBr): 1727, 1637 cm$^{-1}$ (CO).
$^1$H NMR (CDCl$_3$); δ=3.03 (s, 9H), 3.14 (s, 3H), 6.80 (s, 1H), 7.1–7.9 (m, 7H).

What is claimed is:
1. A compound of the formula

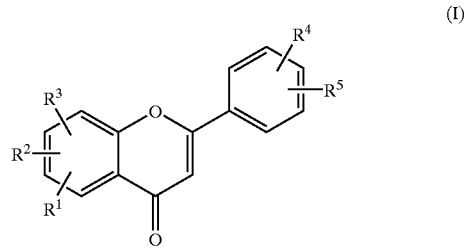

(I)

wherein each of $R^1$, $R^2$, $R^3$, $R^4$ and $R^5$ is a substituent selected from the group consisting of:
hydrogen;
OOCNR$^6$(R$^7$), in which each of R$^6$ and R$^7$ is hydrogen, methyl or ethyl and in which each of R$^6$ and R$^7$ may be the same or different;
OR$^8$, wherein R$^8$ is hydrogen, methyl or ethyl

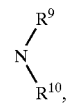

wherein each of R$^9$ and R$^{10}$ is hydrogen or methyl;
a halogen atom selected from the group consisting of fluoride, chloride and iodide;
COOR$^{11}$, wherein R$^{11}$ is hydrogen, sodium, potassium, or an alkyl of one to two carbon atoms;
CONR$^{12}$R$^{13}$, wherein each of R$^{12}$ and R$^{13}$ is hydrogen, methyl or ethyl;
NO$_2$; and
CN; and
wherein at least one of R$^1$, R$^2$, R$^3$, R$^4$ and R$^5$ is OOCNR$^6$(R$^7$) and wherein at least one of R$^4$ and R$^5$ is other than hydrogen.
2. A compound of the formula

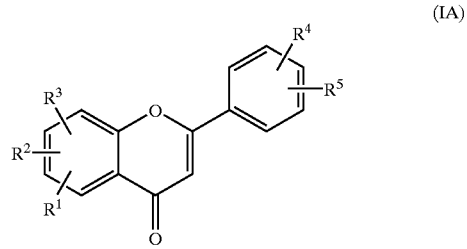

(IA)

wherein R$^4$ is OOCNR$^6$(R$^7$), in which each of R$^6$ and R$^7$ is hydrogen, methyl or ethyl and in which each of R$^6$ and R$^7$ may be the same or different, and wherein R$^4$ occurs in the 2', 3' or 4' position; and wherein each of $R^1$, $R^2$, $R^3$, and $R^5$ is a substituent selected from the group consisting of:

hydrogen;

$OR^8$, wherein $R^8$ is hydrogen, methyl, or ethyl;

wherein each of $R^9$ and $R^{10}$ is hydrogen or methyl;
a halogen atom selected from the group consisting of fluoride, chloride, and iodide;
$COOR^{11}$, wherein $R^{11}$ is hydrogen, sodium, potassium, or an alkyl of one to two carbon atoms;
$CONR^{12}R^{13}$, wherein each of $R^{12}$ and $R^{13}$ is hydrogen, methyl, or ethyl;
$NO_2$; and
CN.

3. A compound of the formula

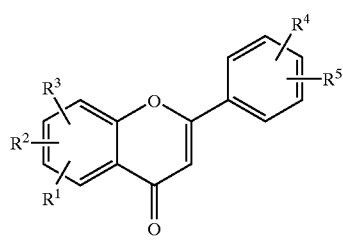

(IB)

wherein $R^1$ is $OOCNR^6(R^7)$, in which each of $R^6$ and $R^7$ is hydrogen, methyl or ethyl and in which each of $R^6$ and $R^7$ may be the same or different; and wherein $R^1$ occurs in the 5, 6, 7, or 8 position; and wherein each of $R^2$, $R^3$, $R^4$ and $R^5$ is a substituent selected from the group consisting of:

hydrogen;

$OR^8$, wherein $R^8$ is hydrogen; methyl; or ethyl;

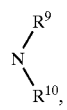

wherein each of $R^9$ and $R^{10}$ is hydrogen or methyl;
a halogen atom selected from the group consisting of fluoride, chloride, and iodide;
$COOR^{11}$,
wherein $R^{11}$ is hydrogen; sodium; potassium; or an alkyl of one to two carbon atoms;
$CONR^{12}R^{13}$, wherein each of $R^{12}$ and $R^{13}$ is hydrogen; methyl; or ethyl;
$NO_2$; and
CN; and wherein at least one of $R^4$ and $R^5$ is other than hydrogen.

4. A compound of the formula

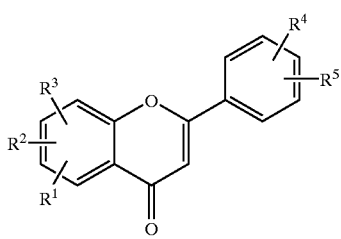

(IC)

wherein each of $R^1$ and $R^4$ is $OOCNR^6(R^7)$ and $R^1$ occurs in the 5, 6, 7, or 8 position and $R^4$ occurs in the 2', 3', or 4' position, and each of $R^6$ and $R^7$ is hydrogen, methyl or ethyl and in which each of $R^6$ and $R^7$ may be the same or different; and wherein each of $R^2$, $R^3$, and $R^5$ is a substituent selected from the group consisting of:

hydrogen;

$OR^8$, wherein $R^8$ is hydrogen, methyl, or ethyl;

wherein each of $R^9$ and $R^{10}$ is hydrogen or methyl;
a halogen atom selected from the group consisting of fluoride, chloride, and iodide;
$COOR^{11}$, wherein $R^{11}$ is hydrogen, sodium, potassium, or an alkyl of one to two carbon atoms;
$CONR^{12}R^{13}$, wherein each of $R^{12}$ and $R^{13}$ is hydrogen, methyl, or ethyl;
$NO_2$; and
CN.

5. A compound of the formula

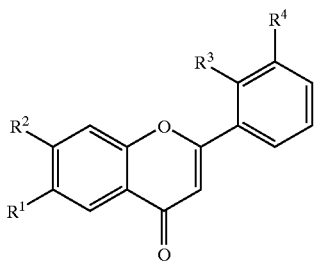

(II)

wherein $R^1$, $R^2$, $R^3$ and $R^4$ are selected from the group consisting of:

hydrogen;

$OOCNR^5(R^6)$, wherein each of $R^5$ and $R^6$ is methyl or ethyl and in which each of $R^5$ and $R^6$ may be the same or different;

OR$^7$, wherein R$^7$ is methyl or ethyl;

wherein each of R$^8$ and R$^9$ is hydrogen or methyl;
a halogen atom selected from the group consisting of fluoride, chloride, and iodide;
COOR$^{10}$, wherein R$^{10}$ is hydrogen, sodium, potassium, or an alkyl of one to two carbon atoms;
CONR$^{11}$R$^{12}$, wherein each of R$^{11}$ and R$^{12}$ is hydrogen, methyl, or ethyl;
NO$_2$; and
CN; and wherein at least one of R$^1$, R$^2$, R$^3$ and R$^4$ is OOCNR$^5$(R$^6$); and wherein at least one of R$^3$ and R$^4$ is other than hydrogen.

6. A compound of the formula

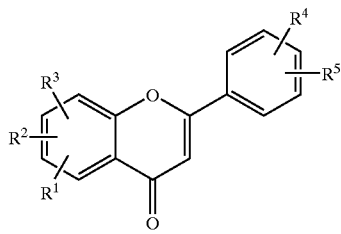

(I)

wherein each of R$^1$, R$^2$, R$^3$, R$^4$ and R$^5$ is a substituent selected from the group consisting of:
hydrogen;
OOCNR$^6$(R$^7$), in which each of R$^6$ and R$^7$ is hydrogen, or a lower alkyl of 1 to 4 carbon atoms and in which each of R$^6$ and R$^7$ may be the same or different;
OR$^8$, wherein R$^8$ is hydrogen, or a lower alkyl of 1 to 4 carbon atoms;

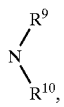

wherein each of R$^9$ and R$^{10}$ is hydrogen or a lower alkyl of 1 to 4 carbon atoms;
a halogen atom selected from the group consisting of fluoride, chloride, bromide and iodide;
COOR$^{11}$, wherein R$^{11}$ is hydrogen, sodium, potassium, or a lower alkyl of 1 to 4 carbon atoms;
CONR$^{12}$R$^{13}$, wherein each of R$^{12}$ and R$^{13}$ is hydrogen or a lower alkyl of 1 to 4 carbon atoms;
NO$_2$; and
CN; and
wherein at least one of R$^1$, R$^2$, R$^3$, R$^4$ and R$^5$ is OOCNR$^6$(R$^7$); and wherein at least one of R$^4$ and R$^5$ is other than hydrogen.

7. The compound of claim 6, wherein each of said a lower alkyl is methyl or ethyl.

8. A pharmaceutical composition comprising a compound of the formula

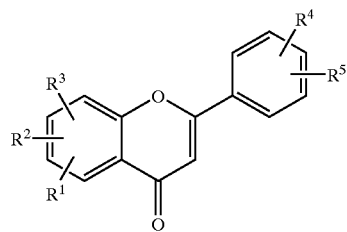

(I)

wherein each of R$^1$, R$^2$, R$^3$, R$^4$ and R$^5$ is a substituent selected from the group consisting of:
hydrogen;
OOCNR$^6$(R$^7$), in which each of R$^6$ and R$^7$ is hydrogen, methyl or ethyl and in which each of R$^6$ and R$^7$ may be the same or different;
OR$^8$, wherein R$^8$ is hydrogen, methyl or ethyl

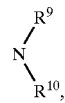

wherein each of R$^9$ and R$^{10}$ is hydrogen or methyl;
a halogen atom selected from the group consisting of fluoride, chloride and iodide;
COOR$^{11}$, wherein R$^{11}$ is hydrogen, sodium, potassium, or an alkyl of one to two carbon atoms;
CONR$^{12}$R$^{13}$, wherein each of R$^{12}$ and R$^{13}$ is hydrogen, methyl or ethyl;
NO$_2$; and
CN; and
wherein at least one of R$^1$, R$^2$, R$^3$, R$^4$ and R$^5$ is OOCNR$^6$(R$^7$); and a pharmaceutically acceptable carrier for said compound.

9. A pharmaceutical composition comprising a compound of the formula

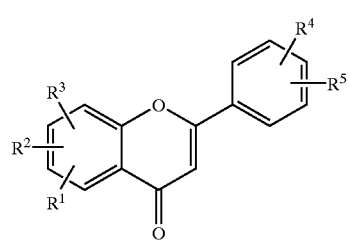

(IA)

wherein R$^4$ is OOCNR$^6$(R$^7$), in which each of R$^6$ and R$^7$ is hydrogen, methyl or ethyl and in which each of R$^6$ and R$^7$ may be the same or different, and wherein R$^4$ occurs in the 2, 3 or 4 position; and
wherein each of R$^1$, R$^2$, R$^3$, and R$^5$ is a substituent selected from the group consisting of:
hydrogen;
OR$^8$, wherein R$^8$ is hydrogen, methyl, or ethyl;

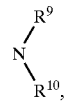

wherein each of R$^9$ and R$^{10}$ hydrogen or methyl;

a halogen atom selected from the group consisting of fluoride, chloride, and iodide;
COOR$^{11}$ wherein R$^{11}$ is hydrogen, sodium, potassium, or an alkyl of one to two carbon atoms;
CONR$^{12}$R$^{13}$, wherein each of R$^{12}$ and R$^{13}$ is hydrogen, methyl, or ethyl;
NO$_2$; and
CN; and a pharmaceutically acceptable carrier for said compound.

10. A pharmaceutical composition comprising a compound of the formula

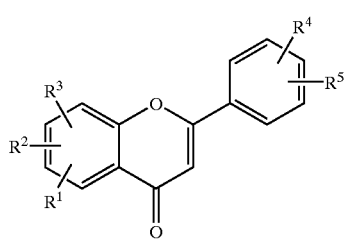

(IB)

wherein
R$^1$ is OOCNR$^6$(R$^7$), in which each of R$^6$ and R$^7$ is hydrogen, methyl or ethyl and in which each of R$^6$ and R$^7$ may be the same or different; and wherein R$^1$ occurs in the 5, 6, 7, or 8 position; and
wherein each of R$^2$, R$^3$, R$^4$ and R$^5$ is a substituent selected from the group consisting of:
hydrogen;
OR$^8$, wherein R$^8$ is hydrogen, methyl, or ethyl;

wherein each of R$^9$ and R$^{10}$ is hydrogen or methyl;
a halogen atom selected from the group consisting of fluoride, chloride, and iodide;
COOR$^{11}$, wherein R$^{11}$ is hydrogen, sodium, potassium, or an alkyl of one to two carbon atoms;
CONR$^{12}$R$^{13}$, wherein each of R$^{12}$ and R$^{13}$ is hydrogen, methyl, or ethyl;
NO$_2$; and
CN; and a pharmaceutically acceptable carrier for said compound.

11. A pharmaceutical composition comprising a compound of the formula

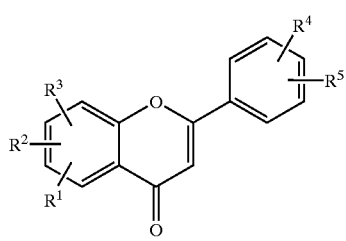

(IC)

wherein each of R$^1$ and R$^4$ is OOCNR$^6$(R$^7$) and R$^1$ occurs in the 5, 6, 7, or 8 position and R$^4$ occurs in the 2, 3, or 4 position, and each of R$^6$ and R$^7$ is hydrogen, methyl or ethyl and in which each of R$^6$ and R$^7$ may be the same or different; and wherein each of R$^2$, R$^3$, and R$^5$ is a substituent selected from the group consisting of:
hydrogen;
OR$^8$, wherein R$^8$ is hydrogen, methyl, or ethyl;

wherein each of R$^9$ and R$^{10}$ is hydrogen or methyl;
a halogen atom selected from the group consisting of fluoride, chloride, and iodide;
COOR$^{11}$, wherein R$^{11}$ is hydrogen, sodium, potassium, or an alkyl of one to two carbon atoms;
CONR$^{12}$R$^{13}$, wherein each of R$^{12}$ and R$^{13}$ is hydrogen, methyl, or ethyl;
NO$_2$; and
CN; and a pharmaceutically acceptable carrier for said compound.

12. A pharmaceutical composition comprising a compound of the formula

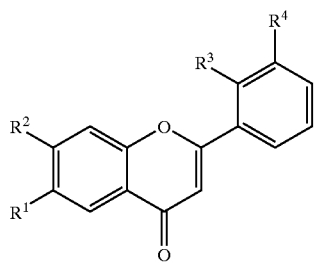

(II)

wherein
R$^1$, R$^2$, R$^3$ and R$^4$ are selected from the group consisting of:
hydrogen;
OOCNR$^5$(R$^6$), wherein each of R$^5$ and R$^6$ is methyl or ethyl and in which each of R$^5$ and R$^6$ may be the same or different;
OR$^7$, wherein R$^7$ methyl or ethyl;

wherein each of R$^8$ and R$^9$ is hydrogen or methyl;
a halogen atom selected from the group consisting of fluoride, chloride, and iodide;
COOR$^{10}$, wherein R$^{10}$ is hydrogen, sodium, potassium, or an alkyl of one to two carbon atoms;
CONR$^{11}$R$^{12}$, wherein each of R$^{11}$ and R$^{12}$ is hydrogen, methyl, or ethyl;
NO$_2$; and
CN; and
wherein at least one of R$^1$, R$^2$, R$^3$ and R$^4$ is OOCNR$^5$(R$^6$); and a pharmaceutically acceptable carrier for said compound.

13. A pharmaceutical composition comprising a compound of the formula $$\text{(I)}$$

wherein each of $R^1$, $R^2$, $R^3$, $R^4$ and $R^5$ is a substituent selected from the group consisting of:
hydrogen;
OOCNR$^6$(R$^7$), in which each of R$^6$ and R$^7$ is hydrogen, or a lower alkyl of 1 to 4 carbon atoms and in which each of R$^6$ and R$^7$ may be the same or different;
OR$^8$, wherein R$^6$ is hydrogen, or a lower alkyl of 1 to 4 carbon atoms;

$$\begin{array}{c} R^9 \\ \diagup \\ N \\ \diagdown \\ R^{10}, \end{array}$$

wherein each of R$^9$ and R$^{10}$ is hydrogen or a lower alkyl of 1 to 4 carbon atoms;
a halogen atom selected from the group consisting of fluoride, chloride, bromide and iodide;
COOR$^{11}$, wherein R$^{11}$ is hydrogen, sodium, potassium, or a lower alkyl of 1 to 4 carbon atoms;
CONR$^{12}$R$^{13}$, wherein each of R$^{12}$ and R$^{13}$ is hydrogen or a lower alkyl of 1 to 4 carbon atoms;
NO$_2$; and
CN; and
wherein at least one of R$^1$, R$^2$, R$^3$, R$^4$ and R$^5$ is OOCNR$^6$ (R$^7$); and a pharmaceutically acceptable carrier for said compound.

14. A method for inhibiting acetylcholine esterase activity by administering; to a host in need of acetylcholine esterase inhibition, an effective therapeutic acetylcholine esterase amount of a compound of the formula $$\text{(I)}$$

wherein each of R$^1$, R$^2$, R$^3$, R$^4$ and R$^5$ is a substituent selected from the group consisting of:
hydrogen;
OOCNR$^6$ (R$^7$), in which each of R$^6$ and R$^7$ is hydrogen, methyl or ethyl and in which each of R$^6$ and R$^7$ may be the same or different;
OR$^8$, wherein R$^8$ is hydrogen, methyl or ethyl $$\begin{array}{c} R^9 \\ \diagup \\ N \\ \diagdown \\ R^{10}, \end{array}$$

wherein each of R$^9$ and R$^{10}$ is hydrogen or methyl;
a halogen atom selected from the group consisting of fluoride, chloride and iodide;
COOR$^{11}$, wherein R$^{11}$ is hydrogen, sodium, potassium, or an alkyl of one to two carbon atoms;
CONR$^{12}$R$^{13}$, wherein each of R$^{12}$ and R$^{13}$ is hydrogen, methyl or ethyl;
NO$_2$; and
CN; and
wherein at least one of R$^1$, R$^2$, R$^3$, R$^4$ and R$^5$ is OOCNR$^6$ (R$^7$).

15. A method for inhibiting acetylcholine esterase activity by administering; to a host in need of acetylcholine esterase inhibition, an effective therapeutic acetylcholine esterase amount of a compound of the formula $$\text{(II)}$$

wherein
R$^1$, R$^2$, R$^3$ and R$^4$ are selected from the group consisting of:
hydrogen;
OOCNR$^5$ (R$^6$), wherein each of R$^5$ and R$^6$ is methyl or ethyl and in which each of R$^5$ and R$^6$ may be the same or different;
OR$^7$, wherein R$^7$ methyl or ethyl;

$$\begin{array}{c} R^8 \\ \diagup \\ N \\ \diagdown \\ R^9, \end{array}$$

wherein each of R$^8$ and R$^9$ is hydrogen or methyl;
a halogen atom selected from the group consisting of fluoride, chloride, and iodide;
COOR$^{10}$, wherein R$^{10}$ is hydrogen, sodium, potassium, or an alkyl of one to two carbon atoms;
CONR$^{11}$ R$^{12}$, wherein each of R$^{11}$ and R$^{12}$ is hydrogen, methyl, or ethyl;
NO$_2$; and
CN; and
wherein at least one of R$^1$, R$^2$, R$^3$ and R$^4$ is OOCNR$^5$ (R$^6$).

16. A method for inhibiting acetylcholine esterase activity by administering; to a host in need of acetylcholine esterase inhibition, an effective therapeutic acetylcholine esterase amount of a compound of the formula

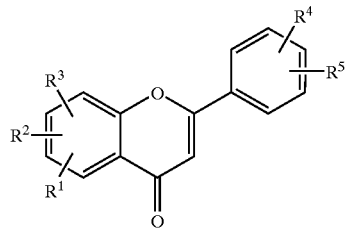

(I)

wherein each of $R^1$, $R^2$, $R^3$, $R^4$ and $R^5$ is a substituent selected from the group consisting of:

hydrogen;

$OOCNR^6 (R^7)$, in which each of $R^6$ and $R^7$ is hydrogen, or a lower alkyl of 1 to 4 carbon atoms and in which each of $R^6$ and $R^7$ may be the same or different;

$OR^8$, wherein $R^8$ is hydrogen, or a lower alkyl of 1 to 4 carbon atoms;

wherein each of $R^9$ and $R^{10}$ is hydrogen or a lower alkyl of 1 to 4 carbon atoms;

a halogen atom selected from the group consisting of fluoride, chloride, bromide and iodide;

$COOR^{11}$, wherein $R^{11}$ is hydrogen, sodium, potassium, or a lower alkyl of 1 to 4 carbon atoms;

$CONR^{12}R^{13}$, wherein each of $R^{12}$ and $R^{13}$ is hydrogen or a lower alkyl of 1 to 4 carbon atoms;

$NO_2$; and

CN; and wherein at least one of $R^1$, $R^2$, $R^3$, $R^4$ and $R^5$ is $OOCNR^6 (R^7)$.

17. A method for producing flavone derivatives of claim 1 comprising providing a 2-hydroxyacetophenone derivative (a);

reacting an aromatic acid chloride with the 2-hydroxyacetophenone derivative (a);

treating a phenolester of formula (b) alkali hydroxide(s) in pyridine to form a 1,3-diketone;

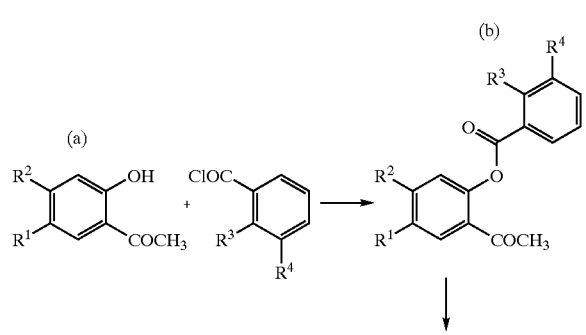

treating (c), in the presence of mineral acid in acetic acid as a solvent, to effect ring closure of the 1,3-diketone (c).

18. The method of claim 17, comprising producing a flavone derivative having at least one alkoxy group; and subjecting said flavone derivative having at least one alkoxy group to a dealkylation resulting in a hydroxy-flavone compound.

19. The method of claim 18, comprising reacting a hydroxyflavone reactant with dialkylcarbamoyl chloride ($R^6R^7$ NCOCl) in the presence of a base selected from the group consisting of sodium hydride and potassium carbonate, according to the following reaction scheme:

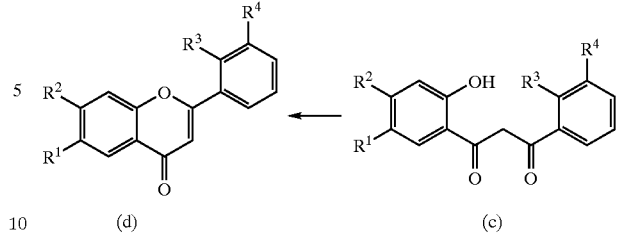

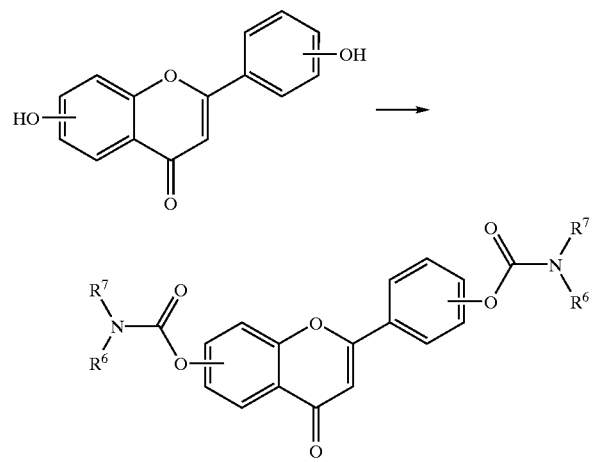

in the presence of an organic solvent selected from the group consisting of dimethylformamide, acetonitrile and a mixture of dimethylformamide and acetonitrile.

20. A compound of claim 1, which is 2'-(N,N-dimethylcarbamoyloxy)flavone.

21. A compound of claim 1, which is 2'-(N-Ethyl-N-methylcarbamoyloxy)flavone.

22. A compound of claim 1, which is 3'-(N,N-Dimethylcarbamoyloxy)flavone.

23. A compound of claim 1, which is 3'-(N-Ethyl-N-methylcarbamoyloxy)flavone.

24. A compound of claim 1, which is 7-Ethoxy-2'-(N,N-dimethylcarbamoyloxy)flavone.

25. A compound of claim 1, which is 7-Ethoxy-2'-(N, N-dimethlylcarbamoyloxy) flavone.

26. A compound of claim 1, which is 7-Ethoxy-2'-(N-ethyl-N-methylcarbamoyloxy) flavone.

27. A compound of claim 1, which is 7-(N,N-Dimethylcarbamoyloxy)-2'-methoxyflavone.

28. A compound of claim 1, which is 7-(N,N-Dimethylcarbamoyloxy)-2'-methoxyflavone.

29. A compound of claim 1, which is 7,2'-Di(N,N-dimethylcarbamoxyloxy)flavone.

30. A compound of claim 1, which is 7,2'-Di(N,N-dimethylcarbamoyloxy)flavone.

31. A compound of claim 1, which is 6-Amino-3'-(N,N-dimethylcarbamoyloxy)flavone.

32. A compound of claim 1, which is 6-Amino-3'-(N,N-dimethylcarbamoyloxy)flavone.

33. A compound of claim 1, which is 6-Dimethylamino-3'-(N,N-dimethylcarbamoyloxy)flavone.

34. A compound of claim 1, which is 6-Dimethylamino-3'-(N,N-dimethylcarbamoyloxy)flavone.

* * * * *